United States Patent [19]

Vitzthum et al.

[11] Patent Number: 4,540,784

[45] Date of Patent: Sep. 10, 1985

[54] RECOVERY OF CAFFEINE ADSORBED TO ACTIVATED CARBON

[75] Inventors: Otto G. Vitzthum, Bremen; Peter Werkhoff, Stuhr; Manfred Gehrig, Wolnzach, all of Fed. Rep. of Germany

[73] Assignee: Hag GF Aktiengesellschaft, Bremen, Fed. Rep. of Germany

[21] Appl. No.: 485,765

[22] Filed: Apr. 18, 1983

[51] Int. Cl.³ .......................................... C07D 473/12
[52] U.S. Cl. .................................... 544/274; 544/275
[58] Field of Search .................... 544/274, 275, 273

[56] References Cited

U.S. PATENT DOCUMENTS 4,298,736 11/1981 Katz et al. ............................ 544/275

FOREIGN PATENT DOCUMENTS 78586 12/1980 German Democratic Rep. .

Primary Examiner—Nicholas S. Rizzo
Attorney, Agent, or Firm—Linn I. Grim; Daniel J. Donovan; Joseph T. Harcarik

[57] ABSTRACT

The invention relates to a process for recovering caffeine adsorbed to activated carbon by treating the loaded activated carbon with formic acid.

4 Claims, No Drawings

RECOVERY OF CAFFEINE ADSORBED TO ACTIVATED CARBON

TECHNICAL FIELD

The invention relates to a process for recovering caffeine from loaded activated carbon which is characterized by treating the loaded activated carbon with formic acid.

BACKGROUND ART

For health reasons vegetable products—mainly coffee—of reduced caffeine content have gained increasing significance. Thus, quite a number of processes have been developed which, in various ways, try to reduce the caffeine concentration. Normally organic solvents have been used for extraction of the hydrolyzed coffee beans. The recovery of the solvent has been effected by distillation, for example, in the course of which the caffeine is obtained as by-product.

In order to avoid any contamination of the vegetable material by solvent residues, carbon dioxide which is unobjectionable under the health aspect has recently been used as extractant (German Pat. Nos. 2,005,293 and 2,212,281). The carbon dioxide solvent in this process is freed from dissolved caffeine by means of activated carbon.

Prior to recycling of spent activated carbon, the adsorbed substances are normally subjected to pyrolysis whereafter the carbon is thermally reactivated. On account of the usefulness of caffeine, such a procedure is uneconomical.

Hence, it is not surprising that efforts are being made to recover the adsorbed caffeine. Measures for desorbing the caffeine must be selected in consideration of the fact that active carbon is a very good adsorbent, a circumstance that renders desorption difficult. Moreover, the use of any agents that are objectionable under the health aspect is to be avoided because the extraction is effected with carbon dioxide for the very purpose of avoiding such agents.

According to the teaching of German OS No. 2,544,116 the adsorbate is desorbed with supercritical gases, especially carbon dioxide. Thereafter the dissolved adsorbate must be removed from the dissolving gas.

According to U.S. Pat. No. 4,298,736 caffeine adsorbed to activated carbon is desorbed with a food-grade liquid solvent which may be an organic acid or an alcohol. Acetic acid, propionic acid and butyric acid are literally mentioned as organic acids. The process is to be carried out preferably at temperatures above 100° C. and the solvents, i.e., the acids, should have a high boiling point.

DISCLOSURE OF THE INVENTION

With the present invention it has been surprisingly found that desorption with formic acid which has a boiling point 18° C. lower than that of acetic acid, the solvent preferred in the U.S. patent, permits considerably better results despite shorter treating periods and lower treating temperatures and the use of smaller amounts of treating acid. This could not be expected from the general teaching given in the U.S. patent. The general teaching disclosed in said U.S. patent rather points toward higher boiling solvents.

The process temperature preferably is within a range between 90° and 100° C. The use of higher temperatures also calls for pressures higher than atmospheric because formic acid boils at about 100° C.

The treating period is preferably within a range of about 2 to 3 hours; an amount of formic acid 10 to 20 times that of activated carbon, based on the weight of the latter, is sufficient. The formic acid may be used in mixture with water, such mixtures containing 22% water at the most, although the use of undiluted formic acid is preferred.

The process can be carried out batch-wise or continuously. Preferably the process of the invention is carried out in battery operation, i.e., the loaded activated carbon is first contacted with formic acid which has already desorbed caffeine in preceding treating stages, and in the last treating stage of the battery the activated carbon already partially freed from caffeine is contacted with fresh formic acid which desorbes all the residual caffeine from the activated carbon. In this way, the caffeine-loaded formic acid is obtained at one end of the battery and activated carbon freed from caffeine is obtained at the other end. After removal of excess solvent by steaming and/or drying the activated carbon can be re-used. The adsorption activity of the activated carbon diminishes slightly with each recycle step. High temperature activation of the carbon is necessary only after repeated recycling.

Separation of the recovered caffeine from the formic acid takes place most simply by distillation of the formic acid.

In the following examples the below indicated mode of operation was adopted:

The formic acid was forced by means of a pump first through a heat exchanger and thereafter through the heated extraction tube. After having passed through a further heat exchanger the formic acid fractions were removed and analyzed.

The rest containers consisted of V4A steel (1.4571=AISI 316). Further, materials for containers resistant to boiling formic acid can be found, for example, in the tables of materials issued by Messrs. Dechema.

In all the tests, the temperature was 100° C.

EXAMPLE 1

50 g of activated carbon having a caffeine content of 10.9% by weight were treated with a flow of 1 kg formic acid for a period of 150 minutes. 91% of the adsorbed caffeine were found in the formic acid. The remainder was still on the activated carbon. The solution had a caffeine concentration of about 0.5%. After half the extraction period, when 0.5 kg of formic acid had been forced through the activated carbon, 78% of the caffeine had been desorbed.

This example permits an impressive comparison with example 1 of the above mentioned U.S. Pat. No. 4,298,736. Thus, in the known process only 73% caffeine were desorbed and recovered after 2 hours of treatment at 117° C. with 10 times the amount of acetic acid, based on the weight of activated carbon. On the other hand, the present example shows that with 10 times the amount of formic acid at a temperature of 100° C. 78% of the caffeine can be desorbed and recovered already after a time of 1¼ hour. The higher yield attained under considerably more favorable process conditions with formic acid in lieu of acetic acid is extraordinarily surprising. The expert could not expect this from the general teaching of the U.S. patent. Rather was it probable that under comparable conditions poorer results would be achieved with formic acid.

EXAMPLE 2

Another 50 g of activated carbon having a caffeine content of 10.9% by weight were extracted with 1 kg formic acid containing 0.5% by weight of caffeine from the preceding example. In this run, further 64% of the adsorbed caffeine were extracted. The solution contained about 0.8% by weight of caffeine.

What is claimed is:

1. A process for recovering caffeine from a caffeine loaded activitated carbon comprising the desorption of said caffeine loaded activated carbon with a formic acid solution comprising at least 78 weight percent formic acid.

2. The process of claim 1 wherein the formic acid solution is an aqueous solution comprising about 78 to about 100 weight percent formic acid.

3. The process of claim 1 wherein the desorption of said caffeine loaded activated carbon is carried out in a battery operation.

4. The process of claim 2 wherein the desorption of said caffeine loaded activated carbon is carried out in a battery operation.

* * * * *